United States Patent [19]

Chen et al.

[11] Patent Number: 5,427,933
[45] Date of Patent: Jun. 27, 1995

[54] REDUCTION OF PHENYLALKYL KETONES TO THE CORRESPONDING (S)-HYDROXY DERIVATIVES USING MUCOR HIEMALIS IFO 5834

[75] Inventors: Shieh-Shung T. Chen, Morganville; Ali Shafiee, Westfield, both of N.J.

[73] Assignee: Merck & Co., Inc., Rahway, N.J.

[21] Appl. No.: 277,727

[22] Filed: Jul. 20, 1994

[51] Int. Cl.$^6$ .......................... C12P 17/12; C12P 7/22; C12N 1/14; C07B 57/00
[52] U.S. Cl. ..................... 435/122; 435/156; 435/254.8; 435/931; 435/280
[58] Field of Search ............ 435/280, 122, 156, 254.8, 435/931

[56] References Cited

U.S. PATENT DOCUMENTS 5,270,324 12/1993 Zamboni et al. ............... 514/311

FOREIGN PATENT DOCUMENTS 604114 6/1994 European Pat. Off.

OTHER PUBLICATIONS

King et al., J. Org. Chem., 1993, 58, 3731–3735.

*Primary Examiner*—David M. Naff
*Assistant Examiner*—Mike Metter
*Attorney, Agent, or Firm*—Mollie M. Yang; David L. Rose

[57] ABSTRACT

A process for reducing a phenylalkyl ketone to the corresponding (S)-hydroxy derivative is disclosed. The process comprises contacting the phenylalkyl ketone with *Mucor hiemalis* IFO 5834 and recovering the (S)-hydroxy derivative.

3 Claims, No Drawings

2

REDUCTION OF PHENYLALKYL KETONES TO THE CORRESPONDING (S)-HYDROXY DERIVATIVES USING MUCOR HIEMALIS IFO 5834

BACKGROUND OF THE INVENTION

The leukotrienes constitute a group of locally acting hormones, produced in living systems from arachidonic acid. The major leukotrienes are leukotriene $B_4$ (abbreviated as $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various disease states are also discussed in the book by Rokach.

There has been reported in U.S. Pat. No. 5,270,324 a class of quinoline type leukotriene antagonists, of which compounds having the formula (I) are a subset:

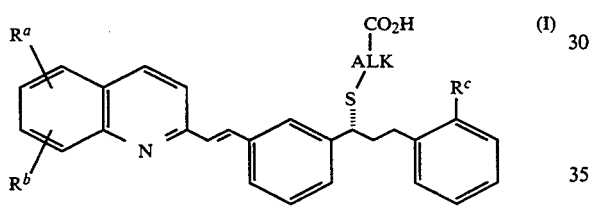

wherein $R^a$, $R^b$ are, inter alia, hydrogen or a halogen; and $R^c$ may be $CO_2R^d$, $COR^d$ or $C(R^e)_2$—OH; $R^d$ may be hydrogen or a lower alkyl, and $R^e$ may be lower alkyl; and ALK is for example cyclopropyl-1,1-(bis)-methylene, isopropyl, and the like.

There is further disclosed in European Published Application 604114 leukotriene antagonists, of which compounds having the formula (II) are a subset:

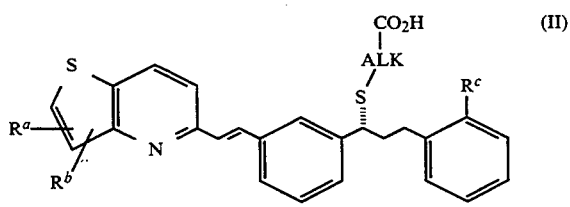

in which $R^a$, $R^b$, $R^c$ and ALK are as given above.

(S)-Hydroxy compounds of formula (IV), infra, are intermediates in the synthesis of compounds of formulae (I) and (II). Compounds of formula (IV) may be prepared from the corresponding ketones of formula (III), infra, by using a chiral reducing agent such as diisopinocampheylchloroborane. The chemical chiral reduction generally requires the use of expensive chiral reducing agents; therefore, there exists a need for an alternative method for the preparation of chiral compounds of formula (IV) that may be more economical and/or more convenient than the chemical method.

SUMMARY OF THE INVENTION

The present invention provides a stereoselective process for reducing a phenylalkyl ketone to the corresponding (S)-hydroxy derivative, which comprises contacting said phenylalkyl ketone with *Mucor hiemalis*.

DETAILED DESCRIPTION OF THE INVENTION

In one aspect, the present invention provides a stereoselective process for reducing a phenylalkyl ketone to the corresponding (S)-hydroxy derivative, which comprises contacting said phenylalkyl ketone with *Mucor hiemalis*.

In a preferred embodiment said phenylalkyl ketone has the formula (III):

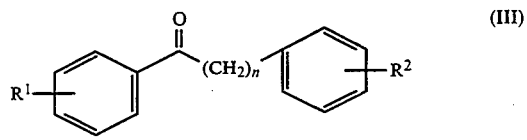

and said (S)-hydroxy derivative has the formula (IV):

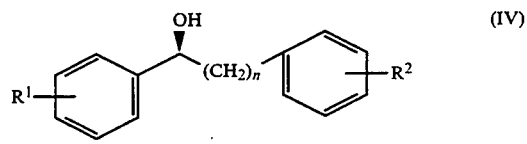

wherein
$R^1$ is hydrogen, halogen, lower alkyl, lower alkoxy, $CO_2R^5$, $COR^5$ or $C(R^6)_2$—O—$R^7$; or a radical of the formula:

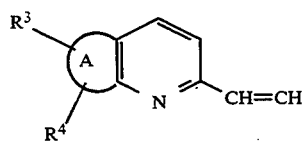

$R^2$ is hydrogen, halogen, lower alkyl, lower alkoxy, $CO_2R^5$, $COR^5$ or $C(R^6)_2$—O—$R^7$;
$R^3$ and $R^4$ are independently hydrogen or halogen; and
$R^5$ is hydrogen or lower alkyl;
$R^6$ is lower alkyl; and
$R^7$ is hydrogen or a hydroxy protecting group.
A is —CH=CH—S— or —CH=CH—CH=CH—;
n is 1 to 3.

In a more preferred embodiment, said phenylalkyl ketone has the formula (IIIa):

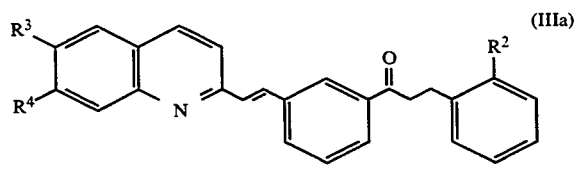

and said (S)-hydroxy derivative has the formula (IV):

-continued

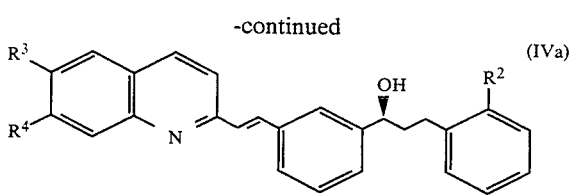

wherein $R^2$ is $CO_2R^5$ or $C(R^6)_2$—O—$R^7$;

$R^3$ is hydrogen and $R^4$ is chlorine; or $R^3$ and $R^4$ each is fluorine;

$R^5$ is hydrogen or lower alkyl;

$R^6$ is lower alkyl; and $R^7$ is hydrogen or a hydroxy protecting group.

More preferably, in compounds of formulae (IIIa) and (IVa) $R^3$ is hydrogen and $R^4$ is chlorine; $R^2$ is $CO_2R^5$; and $R^5$ is methyl.

Abbreviations and Definitions

In the application, unless specifically stated otherwise, the following abbreviations and definitions apply.

FAB-MS=fast atom bombardment mass spectrometry

HPLC=high pressure liquid chromatography

MES=N-morpholinoethanesulfonic acid

NMR=nuclear magnetic resonance

TLC=thin-layer chromatography

UV=ultraviolet

"Alkyl" includes linear, branched and cyclic structures and combinations thereof.

"Lower alkyl" means alkyl groups of from 1 to 7 carbon atoms. Examples of lower alkyl groups include methyl, ethyl, propyl, isopropyl, butyl, s- and t-butyl, pentyl, hexyl, heptyl, cyclopropyl, cyclobutyl, cyclopentylmethyl, cyclohexyl, and the like.

"Halogen" includes fluorine, chlorine, bromine and iodine.

"Hydroxy protecting group" may be for example an ether such as methoxymethyl, tetrahydropyranyl, ethoxyethyl, trichloroethyl, t-butyl, allyl, benzyl, trimethylsilylethyl, diphenylmethyl, and triphenylmethyl; a silyl ether such as trimethylsilyl, dimethylisopropylsilyl, t-butyldimethylsilyl, and t-butyldiphenylsilyl; an ester such as formyl, trichloroacetyl, benzoyl, and trifluoroacetyl; a carbonate such as trichloroethyl, benzyl, and allyl. Other suitable hydroxy protecting groups may be found in standard references such as *Protective Groups in Organic Synthesis*, Green and Wuts, Eds., 1991, John Wiley & Sons, Inc, NY.

Utility

Compounds of formula (IV) are intermediates in the preparation of leukotriene antagonists such as those of formulae (I) and (II); the preparation of leukotriene antagonists using such intermediates are disclosed in U.S. Pat. No. 5,270,324 and EP Published Application 604114, as well as co-pending U.S. application Ser. No. 08/174,931. Leukotriene antagonists such as compounds of formulae (I) and (II) are useful as antiasthmatic, anti-allergic, anti-inflammatory, and cytoprotective therapeutic agents.

Preparation of the Substrate

In the present process for microbial chiral reduction of ketones, the substrates for *Mucor hiemalis*, compounds of formula (III) may be prepared according to methods known in the art. For example, preparation of compounds of formula (IIIa) wherein A is —CH=CH—CH=CH— is disclosed in U.S. Pat. No. 5,270,324; and preparation of compounds of formula (IIIa) wherein A is —S—CH=CH— is disclosed in European Published Application 604114.

Description of the Process

The *Mucor hiemalis* used in the present process was obtained from the collection at the Institute of Fermentation Osaka, 17-85 Juso-Honmachi, 2-Chome, Yodogawaku, Osaka, 532, Japan under the accession number IFO5834.

The *Mucor hiemalis* may be cultivated in a conventional medium containing known nutritional sources for growth of the microorganism, i.e., assimilable sources of carbon and nitrogen, with optional inorganic salts and other known growth factors added. The culture is preferably grown under submerged aerobic conditions; however, surface cultures and bottles may also be used for cultivation on a smaller scale. The general procedures used for the cultivation of other fungi are applicable to the present invention.

The nutrient medium employed for the cultivation of *Mucor hiemalis* should contain an appropriate assimilable carbon source, such as ribose, glucose, fructose, sucrose, and cellobiose. As a nitrogen source, ammonium chloride, ammonium sulfate, urea, ammonium nitrate, sodium nitrate, sodium glutamate, etc., may be used either alone or in combination with organic nitrogen sources, such as peptone, meat extract, yeast extract, corn steep liquor, soybean meal, cotton seed meal, etc. There may also be added, if necessary, nutrient inorganic salts to provide sources of sodium, potassium, calcium, ammonium, phosphate, sulfate, chloride, bromide, carbonate, zinc, magnesium, manganese, cobalt, iron, and the like.

The *Mucor hiemalis* may be grown at any temperature suitable for satisfactory growth, e.g., 25°–40° C., and is most conveniently carried out at a temperature of around 270°–32° C. If fermentation is to be carried out in tank fermentors, it is desirable to use a vegetative inoculum in a nutrient broth from a slant culture or a lyophilized culture. After obtaining an active inoculum in this manner, it is aseptically transferred to the fermentation medium in a tank fermentor. Agitation in the tank fermentor is provided by stirring, and aeration may be achieved by injection of air or oxygen into the agitated mixture.

In one embodiment of the present process the ketone substrate (III) is placed in contact with the *Mucor Hiemalis* being cultivated in an aqueous nutrient medium. The ketone substrate may be added to the *Mucor Hiemalis* culture at any time; but preferably, the substrate is added when sufficient biomass of the microorganism has been achieved. The biomass concentration can be easily monitored, for example by measuring the light absorbance at 660 nm of culture sample using a spectrophotometer. Typically, maximum biomass is reached about 2 to 3 days after inoculation. The bioconversion process may be monitored with conventional methods such as by HPLC followed by spectroscopic techniques. The level of the stereoselective reduction product reaches a maximum about 3 to 4 days after the addition of the substrate. The bioconversion of the ketone substrate to the corresponding (S)-hydroxy compound can be carried out on a continuous basis, for example for up to 500 hours, with the intermittent addition of the ketone substrate. The desired (S)-hydroxy compound thus produced may be recovered from the fermentation broth by any suitable methods for such recovery and separation; examples of these methods include extraction, precipitation, chromatography, and other art recognized conventional techniques.

In another embodiment of the present process, the ketone substrate is placed in contact with *Mucor Hiemalis* in a resting state. Resting cells of *Mucor Hiemalis* are prepared by harvesting growing cells of *Mucor hiemalis*, for example by centrifugation; the harvested cells may also be lyophilized, and then stored at −80° C. for future use. The resting cells are used as a cell suspension in an appropriate buffered solution such as phosphate or Tris buffer (pH 6–8). The ketone substrate is added to the cell suspension, and the mixture is incubated at a temperature of 20° to 40° C. to effect the reduction. Optionally, glucose can be added to the cell suspension to improve the efficiency of the bioconversion. Cells immobilized on support by physical adsorption or entrapment may also be used for the chiral reduction process. Cell immobilization may be achieved using conventional methods, for example, those reported in Karsten, G. and Simon, H., *Appl. Microb. Biotechnol.*, 1993, 38:441–446 and references cited therein.

It is to be understood that, for the biotransformation, the present invention is not limited to the particular organisms mentioned above but includes the use of variants and mutants thereof that retain the ketone reducing capability. Such variants and mutants can be produced from parent strains by various means, such as X-ray radiation, UV-radiation, and chemical mutagens, such as N-methyl-N′-nitro-N-nitrosoguanidine.

The following examples are provided to more fully illustrate the present invention, and are not to be construed as limiting the scope of the invention in any manner.

EXAMPLE 1

Seed culture of *Mucor hiemalis*

A 1.5 ml frozen vial of *Mucor Hiemalis* was allowed to thaw at room temperature and then transferred to a 250 ml Erlenmeyer flask containing 50 ml of KE medium composed of (per liter of medium):

| | |
|---|---|
| 10 g. | dextrin |
| 5 g. | ardamine pH |
| 5 g | NZ amine type E |
| 3 g | beef extract |
| 1 g | dextrose |
| 0.37 g | $K_2HPO_4$ |
| 0.05 g | $MgSO_4$, 7 $H_2O$ |
| q.v. 1 L | deionized water |
| to pH 7.1 | 0.5 g of $CaCO_3$ |

The flask was incubated for overnight at 27° C. on an orbital shaker at 220 rpm.

EXAMPLE 2

Bioconversion of methyl 2-(3-(3-(2-(7-chloro-2-quinolinyl)ethenyl)phenyl)-3-oxopropyl)benzoate (hereinafter ketoester) to methyl 2-(3-(3-(2-(7-chloro-2-quinolinyl)ethenyl)phenyl)-3(S)-hydroxypropyl)benzoate (hereinafter hydroxyester)

A 2-ml aliquot of the seed culture of Example 1 was transferred into a 250-ml baffled flask containing 50 ml of bioconversion medium composed of (per liter of medium):

| | |
|---|---|
| 20 g | glucose |
| 5 g | soya meal |
| 5 g | yeast extract |
| 5 g | NaCl |
| 9.8 g | N-morpholinoethanesulfonic acid (MES) |
| q.v. 1 L | deionized water; pH adjusted to 7.0 |

A solution of the ketoester (5 mg) in acetone (0.5 ml) was added to the medium, and the flask was incubated at 27° C. on a shaker at 220 rpm in the dark. The bioconversion was monitored as follows: At various time intervals, 1 ml sample was taken from the flask and mixed with 1 ml of isopropanol. The resulting mixture was centrifuged after vortexing and an aliquot from the supernatant was examined by HPLC (Whatman Partisil 10 ODS-3 analytical column; eluant: linear gradient of acetonitrile in water (55%–95% in 30 min.); flow rate: 1 ml/min; column temp: 45° C.).

EXAMPLE 3

Isolation and Characterization of Hydroxyester.

After 48 hrs of incubation, the biotransformation broth from 5 flasks were pooled (total 250 ml), and the pH adjusted to 6.0. The broth was centrifuged (20 min. at 3700 rpm) and the supernatant was recovered. The pellet was then suspended in 150 ml methanol and stirred for 30 min. in dark. The suspension thus obtained was centrifuged as above and the supernatant was again recovered. The pellet was extracted once more and the supernatant was pooled with those previously recovered.

The pooled extract was mixed with an equal volume of methylene chloride and, after vigorous shaking, the methylene chloride phase was recovered and dried under reduced pressure. The dried residue was applied on a semi-preparative silica gel plate and the plate was developed in a methylene chloride solvent system. The developed TLC plate was examined under UV light and a major UV-absorbing band with lower Rf value than the substrate was localized. The silica gel in this area was scraped off and was exhaustively extracted with methylene chloride. The extract was concentrated under reduced pressure and filtered.

The filtered extract was further purified by several injections onto a semi-preparative Whatman Partisil 10 ODS-3 (9.4 mm×25 cm) column. This column was developed using similar conditions for the analytical column, except the flow rate was 3 ml/min (see Example 2). HPLC purified fractions were pooled and directly extracted with methylene chloride. Methylene chloride extract was dried over $Na_2SO_4$ and concentrated to dryness under reduced pressure to give 3 mg of the dried final product (direct HPLC quantitation of substrate and product shows between 30–40% conversion based on time of the harvest). NMR and FAB-MS spectral analysis established the product to be methyl 2-(3(S)-3-(2-(7-chloro-2-quinolinyl)ethenyl)phenyl)-3-hydroxy)propyl)benzoate, and chiral chromatography of HPLC purified fraction on Chiralcel OD column (eluant: 90% hexanes/isopropanol; flow rate: 2 ml/min; retention times: 17.9 min for (S)-hydroxyester, 19.8 min for (R)-hydroxyester) indicated an enantiomeric excess of 90%.

EXAMPLE 4

Bioconversion of Ketoester to Hydroxyester Using Resting Cells of *Mucor hiemalis*

Culture of *Mucor Hiemalis* was grown according to the procedure described in Examples 1 and 2. Culture in the bioconversion medium was incubated for 60 hrs at 28° C. on an orbital shaker at 220 rpm, the cells were harvested by centrifugation at 15,000 rpm for 30 min. The resulting pellet was washed three times with 0.1M phosphate buffer, pH 7.2, lyophilized and stored at −80° C.

The cells were thawed, suspended in 10:50 g/volume of buffer, and the ketoester (2.5 mg/0.5 ml acetone was added to the cell suspension. The mixture was incubated at 27° C. The bioconversion was monitored as described above. After 44 hours of incubation greater than 25% conversion was observed (as determined by HPLC).

EXAMPLE 5

Bioconversion of methyl 2-[3-(3-bromophenyl)-3-oxo-propyl]benzoate to methyl 2-[3-(3-bromophenyl)-3(S)-hydroxypropyl]benzoate The procedure of Example 2 was followed with the exception that the ketoester used therein was replaced by methyl 2-[3-(3-bromophenyl)-3-oxopropyl]benzoate. After incubation for 44 hours, over 90% conversion to the (S)-hydroxy derivative was achieved with entiomeric purity of >96%.

EXAMPLE 6

Bioconversion of methyl 2-(3-(3-(2-(7-fluoro-2-quinolinyl)ethenyl)phenyl)-3-oxopropyl)benzoate to methyl 2-(3-(3-(2-(7-fluoro-2-quinolinyl)ethenyl)-phenyl)-3(S)-hydroxypropyl)benzoate The procedure described in Example 1 was followed except the title ketone substrate (25 mg in 1 ml dimethylsulfoxide) was used in place of the ketoester of Example 1. After 48 hrs. of incubation, a 5% conversion of the title ketone to the title (S)-hydroxy compound was observed.

What is claimed is:

1. A process for reducing a phenylalkyl ketone to the corresponding (S)-hydroxy derivative, which comprises contacting said phenylalkyl ketone with *Mucor hiemalis* IFO 5834 and recovering said (S)-hydroxy derivative, wherein said phenylalkyl ketone has the formula:

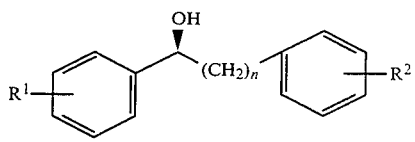

and said (S)-hydroxy derivative has the formula:

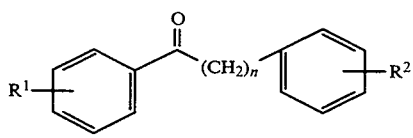

wherein
R$^1$ is hydrogen, halogen, lower alkyl, lower alkoxy, CO$_2$R$^5$, COR$^5$ or C(R$^6$)$_2$—O—R$^7$; or a radical of the formula:

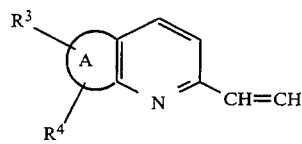

R$^2$ is hydrogen, halogen, lower alkyl, lower alkoxy, CO$_2$R$^5$, COR$^5$ or C(R$^6$)$_2$—O—R$^7$;
R$^3$ and R$^4$ are independently hydrogen or halogen; and
R$^5$ is hydrogen or lower alkyl;
R$^6$ is lower alkyl; and
R$^7$ is hydrogen or a hydroxy protecting group.
A is —CH=CH—S— or —CH=CH—CH=CH—;
n is 1 to 3.

2. A process of claim 1 wherein said phenylalkyl ketone has the formula:

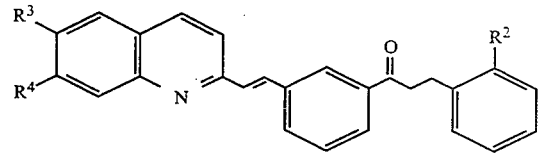

and said (S)-hydroxy derivative has the formula:

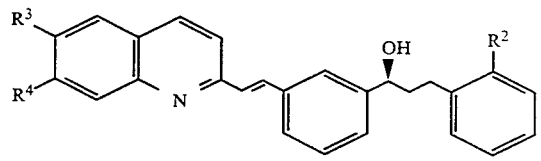

wherein
R$^2$ is CO$_2$R$^5$ or C(R$^6$)$_2$—O—R$^7$;
R$^3$ is hydrogen and R$^4$ is chlorine; or
R$^3$ and R$^4$ each is fluorine;
R$^5$ is hydrogen or lower alkyl;
R$^6$ is lower alkyl; and
R$^7$ is hydrogen or a hydroxy protecting group.

3. A process of claim 2 wherein R$^3$ is hydrogen and R$^4$ is chlorine; R$^2$ is CO$_2$R$^5$; and R$^5$ is methyl.

* * * * *